(12) United States Patent
Holmberg (10) Patent No.: US 11,894,163 B2
(45) Date of Patent: Feb. 6, 2024

(54) FERRULE FOR NON-PLANAR MEDICAL DEVICE HOUSING

(71) Applicant: Heraeus Medical Components LLC, St. Paul, MN (US)

(72) Inventor: Harold Holmberg, St. Paul, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 593 days.

(21) Appl. No.: 17/181,329

(22) Filed: Feb. 22, 2021

(65) Prior Publication Data
US 2021/0265084 A1    Aug. 26, 2021

Related U.S. Application Data

(60) Provisional application No. 62/979,572, filed on Feb. 21, 2020.

(51) Int. Cl.
| | | |
|---|---|---|
| H01B 17/58 | (2006.01) | |
| A61N 1/375 | (2006.01) | |
| H05K 5/02 | (2006.01) | |

(52) U.S. Cl.
CPC ........... *H01B 17/58* (2013.01); *A61N 1/3754* (2013.01); *H05K 5/0247* (2013.01)

(58) Field of Classification Search
None
See application file for complete search history.

(56) References Cited

U.S. PATENT DOCUMENTS

| | | |
|---|---|---|
| 3,979,187 A | 9/1976 | Scherer |
| 4,152,540 A | 5/1979 | Duncan et al. |

(Continued)

FOREIGN PATENT DOCUMENTS

| | | |
|---|---|---|
| CN | 102614588 | 8/2012 |
| CN | 102872529 | 1/2013 |

(Continued)

OTHER PUBLICATIONS

Hussain, et al., "Electrical conductivity of an insulator matrix (alumina) and conductor particle (molybdenum) composites", Journal of the European Ceramic Society, vol. 23, Issue 2, Feb. 2003, pp. 315-321.

(Continued)

*Primary Examiner* — Xanthia C Relford
*Assistant Examiner* — Xanthia C Cunningham
(74) *Attorney, Agent, or Firm* — Dicke, Billig & Czaja, PLLC (57) ABSTRACT

One example provides a ferrule for an implantable medical device including a frame body having an upper surface and an opposing lower surface, an interior perimeter surface extending between the upper and lower surfaces for attachment to an insulator body, and an exterior perimeter surface extending between the upper and lower surfaces for attachment to a housing. A flange extends from the exterior perimeter surface and has an upper surface facing the upper surface of the frame body, the upper surface of the flange to engage an interior surface of a housing of the implantable medical device to limit a position of the housing along the exterior perimeter surface in a direction toward the bottom surface of the frame body, wherein a distance of the top surface of the flange from the top surface of the frame body is greater than and proportional to a thickness of the housing.

15 Claims, 10 Drawing Sheets

(56) References Cited

U.S. PATENT DOCUMENTS

| | | |
|---|---|---|
| 4,217,137 A | 8/1980 | Kraska et al. |
| 4,315,054 A | 2/1982 | Sack et al. |
| 4,352,951 A | 10/1982 | Kyle |
| 4,354,964 A | 10/1982 | Hing et al. |
| 4,362,792 A | 12/1982 | Bowsky et al. |
| 4,456,786 A | 6/1984 | Kyle |
| 4,488,673 A | 12/1984 | Hopper, Jr. |
| 4,602,956 A | 7/1986 | Partlow et al. |
| 4,678,868 A | 7/1987 | Kraska et al. |
| 4,737,601 A | 4/1988 | Gartzke |
| 4,774,953 A | 10/1988 | Foote |
| 4,782,209 A | 11/1988 | Caers et al. |
| 4,816,621 A | 3/1989 | Huebner et al. |
| 4,991,582 A | 2/1991 | Byers et al. |
| 4,992,910 A | 2/1991 | Evans |
| 5,043,535 A | 8/1991 | Lin |
| 5,046,262 A | 9/1991 | Kerbaugh |
| 5,245,999 A | 9/1993 | Dahlberg et al. |
| 5,272,283 A | 12/1993 | Kuzma |
| 5,306,891 A | 4/1994 | Fleming et al. |
| 5,333,095 A * | 7/1994 | Stevenson ............ A61N 1/3754 333/182 |
| 5,407,119 A | 4/1995 | Churchill et al. |
| 5,408,066 A | 4/1995 | Trapani et al. |
| 5,513,793 A | 5/1996 | Malmgren |
| 5,515,604 A | 5/1996 | Horine et al. |
| 5,654,106 A | 8/1997 | Purnell et al. |
| 5,683,435 A | 11/1997 | Truex et al. |
| 5,693,580 A | 12/1997 | Brow et al. |
| 5,738,270 A | 4/1998 | Malmgren |
| 5,750,926 A | 5/1998 | Schulman et al. |
| 5,769,874 A | 6/1998 | Dahlberg |
| 5,782,891 A | 7/1998 | Hassler et al. |
| 5,796,019 A | 8/1998 | Lupton et al. |
| 5,821,011 A | 10/1998 | Taylor et al. |
| 5,851,222 A | 12/1998 | Taylor et al. |
| 5,855,711 A | 1/1999 | Araki et al. |
| 5,861,714 A | 1/1999 | Wei et al. |
| 5,866,851 A | 2/1999 | Taylor et al. |
| 5,867,361 A | 2/1999 | Wolf |
| 5,870,272 A | 2/1999 | Seifried et al. |
| 5,902,326 A | 5/1999 | Lessar |
| 5,905,627 A | 5/1999 | Brendel et al. |
| 6,093,476 A | 7/2000 | Horiuchi et al. |
| 6,232,004 B1 | 5/2001 | Lasater |
| 6,275,369 B1 | 8/2001 | Stevenson et al. |
| 6,284,080 B1 | 9/2001 | Haq et al. |
| 6,414,835 B1 | 7/2002 | Wolf et al. |
| 6,490,148 B1 | 12/2002 | Allen et al. |
| 6,579,492 B2 | 6/2003 | Wehler |
| 6,586,675 B1 | 7/2003 | Bealka et al. |
| 6,643,903 B2 | 11/2003 | Stevenson et al. |
| 6,660,116 B2 | 12/2003 | Wolf et al. |
| 6,765,779 B2 | 7/2004 | Stevenson et al. |
| 6,768,629 B1 | 7/2004 | Allen et al. |
| 6,985,347 B2 | 1/2006 | Stevenson et al. |
| 6,999,818 B2 | 2/2006 | Stevenson et al. |
| 7,035,076 B1 | 4/2006 | Stevenson |
| 7,035,077 B2 | 4/2006 | Brendel |
| 7,038,900 B2 | 5/2006 | Stevenson et al. |
| 7,068,491 B1 | 6/2006 | Burdon et al. |
| 7,107,099 B1 | 9/2006 | O'Phelan et al. |
| 7,136,273 B2 | 11/2006 | Stevenson et al. |
| 7,145,076 B2 | 12/2006 | Knappen et al. |
| 7,174,219 B2 | 2/2007 | Wahlstrand et al. |
| 7,174,223 B2 | 2/2007 | Dalton et al. |
| 7,222,419 B2 | 5/2007 | Horng et al. |
| 7,260,434 B1 | 8/2007 | Lim et al. |
| 7,274,963 B2 | 9/2007 | Spadgenske |
| 7,437,817 B2 | 10/2008 | Zhang et al. |
| 7,480,988 B2 | 1/2009 | Ok et al. |
| 7,502,217 B2 * | 3/2009 | Zhao ...................... H01G 4/35 361/306.1 |
| 7,561,917 B2 | 7/2009 | Wegrzyn, III et al. |
| 7,564,674 B2 | 7/2009 | Frysz et al. |
| 7,569,452 B2 | 8/2009 | Fu et al. |
| 7,630,768 B1 * | 12/2009 | Coffed ................ A61N 1/3752 607/37 |
| 7,668,597 B2 | 2/2010 | Engmark et al. |
| 7,693,576 B1 * | 4/2010 | Lavie .................. A61N 1/3754 607/38 |
| 7,706,124 B2 | 4/2010 | Zhao et al. |
| 7,720,538 B2 | 5/2010 | Janzig et al. |
| 7,725,190 B2 | 5/2010 | Iyer |
| 7,736,191 B1 | 6/2010 | Sochor |
| 7,742,817 B2 | 6/2010 | Malinowski et al. |
| 7,747,321 B2 | 6/2010 | Fischbach et al. |
| 7,761,165 B1 | 7/2010 | He et al. |
| 7,765,005 B2 | 7/2010 | Stevenson |
| 7,794,256 B1 | 9/2010 | Sochor |
| 7,818,876 B2 | 10/2010 | Suaning |
| 7,901,761 B1 | 3/2011 | Jiang et al. |
| 7,930,032 B2 | 4/2011 | Teske et al. |
| 7,970,474 B2 | 6/2011 | Starke |
| 7,989,080 B2 | 8/2011 | Greenberg et al. |
| 8,000,804 B1 | 8/2011 | Wessendorf et al. |
| 8,065,009 B2 | 11/2011 | Biggs |
| 8,131,369 B2 | 3/2012 | Taylor et al. |
| 8,131,376 B1 | 3/2012 | Faraji et al. |
| 8,155,743 B2 | 4/2012 | Rundle et al. |
| 8,163,397 B2 | 4/2012 | Ok et al. |
| 8,179,658 B2 * | 5/2012 | Brendel ............... A61N 1/3754 361/301.2 |
| 8,189,333 B2 | 5/2012 | Foster |
| 8,288,654 B2 | 10/2012 | Taylor et al. |
| 8,346,362 B2 | 1/2013 | Kinney et al. |
| 8,355,785 B1 | 1/2013 | Hammond et al. |
| 8,373,965 B2 | 2/2013 | Iyer |
| 8,391,983 B2 | 3/2013 | Lim |
| 8,494,635 B2 | 7/2013 | Troetzschel et al. |
| 8,497,435 B2 | 7/2013 | Nagata et al. |
| 8,528,201 B2 | 9/2013 | Troetzschel et al. |
| 8,552,311 B2 | 10/2013 | Koester et al. |
| 8,604,341 B2 | 12/2013 | Barry et al. |
| 8,653,384 B2 | 2/2014 | Tang |
| 8,656,736 B2 | 2/2014 | Terao |
| 8,659,870 B2 | 2/2014 | Brendel et al. |
| 8,742,268 B2 | 6/2014 | Reisinger et al. |
| 8,755,887 B2 | 6/2014 | Troetzschel et al. |
| 8,825,162 B2 | 9/2014 | Reisinger |
| 8,886,320 B2 | 11/2014 | Troetzschel et al. |
| 8,894,914 B2 | 11/2014 | Pavlovic |
| 8,929,987 B2 | 1/2015 | Troetzschel et al. |
| 9,431,801 B2 | 8/2016 | Markham et al. |
| 9,478,959 B2 | 10/2016 | Markham et al. |
| 9,653,893 B2 | 5/2017 | Markham et al. |
| 10,418,798 B2 | 9/2019 | Markham et al. |
| 10,770,879 B2 | 9/2020 | Markham et al. |
| 2001/0013756 A1 | 8/2001 | Mori et al. |
| 2001/0018012 A1 | 8/2001 | Harmand et al. |
| 2001/0034966 A1 | 11/2001 | Golubkov et al. |
| 2001/0041227 A1 | 11/2001 | Hislop |
| 2001/0050837 A1 | 12/2001 | Stevenson et al. |
| 2002/0139556 A1 | 10/2002 | Ok et al. |
| 2002/0166739 A1 | 11/2002 | Naerheim |
| 2003/0109903 A1 | 6/2003 | Berrang et al. |
| 2004/0023101 A1 | 2/2004 | Jacobson et al. |
| 2004/0116976 A1 | 6/2004 | Spadgenske |
| 2004/0128016 A1 | 7/2004 | Stewart |
| 2006/0025866 A1 | 2/2006 | Serafin et al. |
| 2006/0247714 A1 | 11/2006 | Taylor et al. |
| 2006/0259093 A1 | 11/2006 | Stevenson et al. |
| 2007/0041164 A1 | 2/2007 | Greenberg et al. |
| 2007/0150020 A1 | 6/2007 | Hokanson et al. |
| 2007/0183118 A1 | 8/2007 | Fu et al. |
| 2007/0217121 A1 | 9/2007 | Fu et al. |
| 2007/0276389 A1 | 11/2007 | Franke et al. |
| 2008/0060834 A1 | 3/2008 | Eck et al. |
| 2008/0071313 A1 | 3/2008 | Stevenson et al. |
| 2008/0119906 A1 | 5/2008 | Starke |
| 2008/0203917 A1 | 8/2008 | Maya |
| 2008/0269831 A1 | 10/2008 | Erickson |
| 2009/0192578 A1 | 7/2009 | Biggs |
| 2009/0281586 A1 | 11/2009 | Lim |

(56) References Cited

U.S. PATENT DOCUMENTS

| | | |
|---|---|---|
| 2010/0023086 A1 | 1/2010 | Lim |
| 2010/0109966 A1 | 5/2010 | Mateychuk et al. |
| 2010/0121438 A1 | 5/2010 | Jarvik |
| 2010/0202096 A1 | 8/2010 | Iyer |
| 2010/0241206 A1* | 9/2010 | Truex .................. A61B 5/7203 607/116 |
| 2010/0258342 A1 | 10/2010 | Parker |
| 2010/0258540 A1 | 10/2010 | Tamura et al. |
| 2011/0032658 A1 | 2/2011 | Iyer |
| 2011/0034965 A1 | 2/2011 | Troetzschel et al. |
| 2011/0034966 A1 | 2/2011 | Troetzschel et al. |
| 2011/0048770 A1 | 3/2011 | Reiterer et al. |
| 2011/0094768 A1 | 4/2011 | Davis et al. |
| 2011/0106228 A1 | 5/2011 | Reiterer et al. |
| 2011/0108320 A1 | 5/2011 | Lakner |
| 2011/0186349 A1 | 8/2011 | Troetzschel et al. |
| 2011/0190885 A1 | 8/2011 | Troetzschel et al. |
| 2011/0232961 A1 | 9/2011 | Teske |
| 2011/0232962 A1* | 9/2011 | Teske .................. A61N 1/3754 174/650 |
| 2012/0006576 A1 | 1/2012 | Barry et al. |
| 2012/0127627 A1 | 5/2012 | Brendel et al. |
| 2012/0193117 A1 | 8/2012 | Specht et al. |
| 2012/0193118 A1 | 8/2012 | Kempf et al. |
| 2012/0193119 A1* | 8/2012 | Kempf ................ A61N 1/3754 174/50.53 |
| 2012/0193125 A1 | 8/2012 | Pavlovic et al. |
| 2012/0193141 A1 | 8/2012 | Reisinger et al. |
| 2012/0194981 A1 | 8/2012 | Kempf et al. |
| 2012/0197326 A1* | 8/2012 | Pavlovic ............... H01R 43/20 607/9 |
| 2012/0197327 A1 | 8/2012 | Specht |
| 2012/0197335 A1 | 8/2012 | Reisinger |
| 2012/0197368 A1 | 8/2012 | Reisinger |
| 2012/0200011 A1 | 8/2012 | Pavlovic |
| 2012/0203294 A1 | 8/2012 | Troetzschel |
| 2012/0209100 A1 | 8/2012 | De Beeck et al. |
| 2012/0309237 A1 | 12/2012 | Marzano |
| 2013/0035733 A1 | 2/2013 | Breyen et al. |
| 2013/0058003 A1* | 3/2013 | Iyer .................... H03H 7/0138 361/302 |
| 2013/0060312 A1* | 3/2013 | Iyer .................... H05K 13/00 607/116 |
| 2013/0184797 A1 | 7/2013 | Tang et al. |
| 2013/0299233 A1 | 11/2013 | Troetzschel et al. |
| 2014/0008121 A1 | 1/2014 | Troetzschel et al. |
| 2014/0144014 A1 | 5/2014 | Troetzschel et al. |
| 2014/0151114 A1 | 6/2014 | Morioka |
| 2014/0262493 A1 | 9/2014 | Markham et al. |
| 2014/0262494 A1 | 9/2014 | Reisinger et al. |
| 2014/0345934 A1 | 11/2014 | Markham et al. |
| 2014/0368298 A1 | 12/2014 | Reisinger |
| 2015/0165220 A1* | 6/2015 | Markham ............ B23K 1/0016 607/116 |
| 2016/0126712 A1 | 5/2016 | Markham et al. |
| 2016/0271400 A1* | 9/2016 | Kronmueller .......... H01B 17/26 |
| 2016/0358699 A1 | 12/2016 | Stevenson et al. |
| 2018/0126175 A1* | 5/2018 | Seitz ...................... H01G 4/35 |
| 2019/0290921 A1 | 9/2019 | Stevenson |
| 2021/0260385 A1 | 8/2021 | Holmberg |

FOREIGN PATENT DOCUMENTS

| | | |
|---|---|---|
| DE | 69729719 | 7/2005 |
| DE | 102006054249 | 5/2008 |
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| EP | 0877400 | 11/1998 |
| EP | 0916364 | 5/1999 |
| EP | 1685874 | 8/2006 |
| EP | 1754511 | 2/2007 |
| EP | 2398026 | 12/2011 |
| JP | H1-148760 | 6/1989 |
| JP | H2-133378 | 5/1990 |
| WO | 03073450 | 9/2003 |
| WO | 2004110555 | 12/2004 |
| WO | 2008103166 | 8/2008 |
| WO | 2010091435 | 8/2010 |
| WO | 2013075797 | 5/2013 |

OTHER PUBLICATIONS

Gil et al., "Grain Growth Kinetics of Pure Titanium," Scripta Metallurgica et Materialia, vol. 33, No. 8, pp. 1361-1366 (Oct. 15, 1995).

Exner, Horst et al., "Laser Joining of Ceramics in Liquid Phase," pp. 1-8 (Nov. 8, 2011).

* cited by examiner

FERRULE FOR NON-PLANAR MEDICAL DEVICE HOUSING

CROSS-REFERENCE TO RELATED APPLICATION

This Non-Provisional patent application claims the benefit of the filing date of U.S. Provisional patent application Ser. No. 62/979,572, filed Feb. 21, 2020, ENTITLED "FERRULE FOR NON-PLANAR MEDICAL DEVICE HOUSING," which is incorporated herein by reference.

BACKGROUND

Implantable medical devices, such as cardiac pacemakers, cardiac defibrillators, and neurostimulators, receive and/or deliver electrical signals to/from portions of a biological body (e.g., human body) via sensing and/or stimulating leads. Implantable medical devices typically include a metal housing (e.g., titanium) having a hermetically sealed interior space which isolates internal circuitry, connections, power sources, and other device components from body fluids. A feedthrough device (often referred to simply as a feedthrough) establishes electrical connections between the hermetically sealed interior space and the exterior bodily fluid side of the device.

Feedthroughs typically include an insulator (e.g., a ceramic material) and electrical conductors or feedthrough pins which extend through the insulator to provide electrical pathways between the exterior and the hermetically sealed interior. A frame-like metal ferrule is disposed about a perimeter surface of the insulator, with the ferrule and insulator being joined to one another, such as by a brazing or soldering process, for example. The ferrule, in-turn, is arranged to fit within a corresponding opening in the metal housing and is attached thereto, typically via welding (e.g., laser welding), to form a hermetic seal, where the insulator serves to electrically insulate the feedthrough pins from one another and from the metal ferrule and housing.

However, non-planarity of the housing surface about the opening in which the feedthrough device is mounted may result in a weld failure between the ferrule and housing such that a hermetic seal is not achieved. For these and other reasons there is a need for a ferrule in accordance with the teachings of the disclosure.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the invention. The following detailed description, therefore, is not to be taken in a limiting sense, and the scope of the invention is defined by the appended claims.

It is to be understood that the features of the various exemplary embodiments described herein may be combined with each other, unless specifically noted otherwise.

Figure 1:
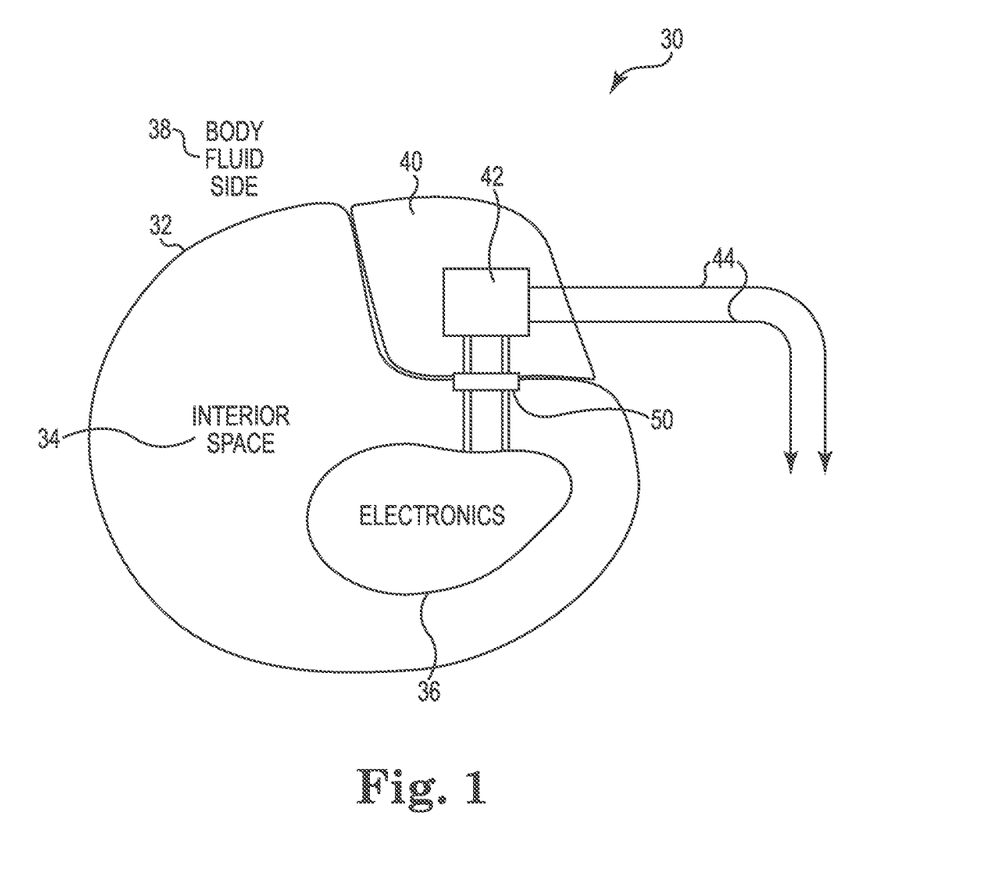
FIG. 1 is a block and schematic diagram generally illustrating an example of an implantable medical device, according to one example.

FIG. 1 is a block and schematic diagram generally illustrating an example of an implantable medical device 30 (e.g., a cardiac pacemaker) suitable for employing a feedthrough device including a ferrule in accordance with examples of the disclosure. Implantable medical device 30 includes a hermetically sealed metal case or housing 32, typically formed of titanium, which defines a hermetically sealed interior space 34 in which device electronics 36 are disposed and protected from fluids of the body fluid side 38 external to housing 32. A header 40 attaches to housing 32 and includes a connector block 42 which typically includes one or more sockets for connecting to one or more sensing and/or stimulating leads 44 that extend between implantable medical device 30 and desired regions of the body (e.g., the human heart and brain). A feedthrough device 50 establishes electrical pathways or connections through housing 32 that maintain the integrity of hermetically sealed interior space 34 and provide electrical connection of leads 44 to internal device electronics 36.

Figure 2A:
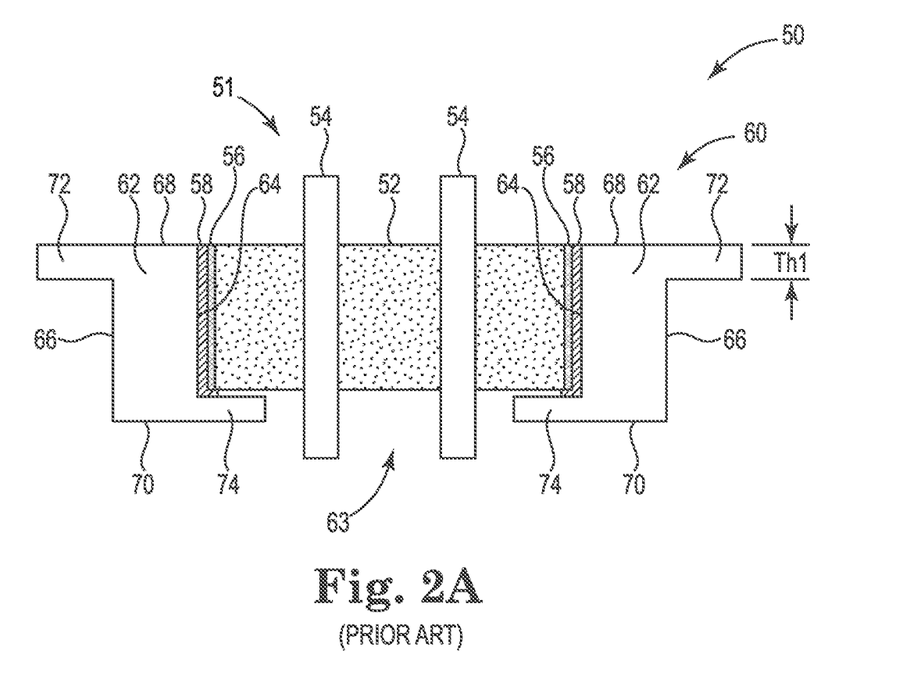
FIG. 2A is a cross-sectional view generally illustrating an example of a known feedthrough device for an implantable medical device.

FIG. 2A is a cross-sectional view generally illustrating an example of a known feedthrough device 50, such as for use with medical device 30 of FIG. 1. Feedthrough device 50 includes an insulator assembly 51 having an insulator body 52 through which a number of feedthrough pins or conducting elements 54 pass, and an example of a known ferrule 60 for connecting to insulator body 52 and for connecting feedthrough device 50 to housing 32 of medical device 30. Ferrule 60 comprises a bio-compatible material, such as titanium, which is to be mechanically and hermetically attached to housing 32, such as by laser welding, or similar techniques (see FIGS. 2B and 2C, for example).

According to one example, ferrule 60 includes a metal frame body 62 having an interior perimeter wall or surface 64, an exterior perimeter wall or surface 66, an upper perimeter surface 68 (to face body fluid side 38, see FIG. 1), and a lower perimeter surface 70 (to face interior space 34). Although not illustrated by the cross-sectional view of FIG. 2A, metal frame body 62 is a continuous ring-like or frame-like structure having any suitable geometric shape (e.g., circular, oval, rectangular, etc.), with interior perimeter surface 64 defining an interior opening 63 which is configured to receive insulator assembly 51. Ferrule 60 includes a housing flange 72 which extends outwardly from exterior perimeter surface 66 (away from interior opening 63), where housing flange 72 is to be welded (such as via laser welding) to housing 32 of implantable medical device 30 (see FIGS. 2B and 2C). Ferrule 60 further includes an insulator flange 74 extending perpendicularly inwardly from interior perimeter surface 64 (toward interior opening 63) to assist in the connection of insulator assembly 51 to ferrule 60.

As described above, conducting elements, or vias, 54 pass through insulator body 52 in a hermetically sealed fashion to transmit electrical signals between the external body fluid side 38 of housing 32 to hermetically sealed interior space 34. Insulator body 52 is formed of a non-electrically conductive material, such as a ceramic material (e.g., aluminum oxide ($Al_2O_3$)), for example, and serves to electrically isolate conducting elements 54 from one another and from ferrule 60 (and housing 32). In one example, a perimeter surface of insulator body 52 is metalized (through a sputter coating process, for example) to provide a thin metal coating 56 thereon. In one example, ferrule 60 is joined to insulator 52 via metal coating 56 using a braze 58, such as of gold, for example, to form a biocompatible and hermetic seal there between.

Figure 2B:
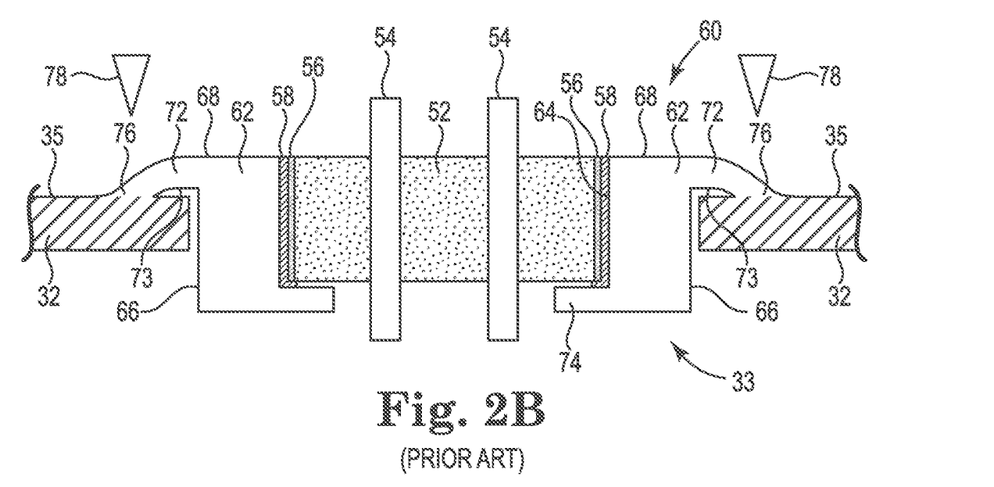
FIG. 2B is a cross-sectional view generally illustrating welding of a known feedthrough device to an implantable medical device.

FIG. 2B is a cross-sectional view illustrating an example of the attachment of feedthrough device 50 to housing 32 via laser welding housing, as indicated by lasers 78. According to one example, as illustrated, feedthrough device 50 is first positioned within an opening 33 in housing 32 such that a lower surface 73 of flange 72 faces exterior surface 35 of housing 32. Laser 78 then melts portions of housing flange 72 and housing 32 such that, upon cooling, the molten portions join together and solidify to form a weld 76 that creates a hermetic seal between ferrule 60 and housing 32 about the exterior perimeter of ferrule 60. Such a weld 76 between overlapping portions of housing 32 and flange 72 is sometimes referred to as a "lap-weld". In one example, both ferrule 60 and housing 32 may be made of titanium. However, other suitable biocompatible and weld-compatible materials may be employed.

While lap-welding is effective to hermetically join housing 32 to flange 62 when the surface 35 of housing 32 about opening 33 is substantially planar, such as illustrated by FIG. 2B, portions of lap-weld 76 about a perimeter of ferrule 60 may fail if the non-planarity of housing surface 35 about opening 33 exceeds a tolerance level.

Figure 2C:
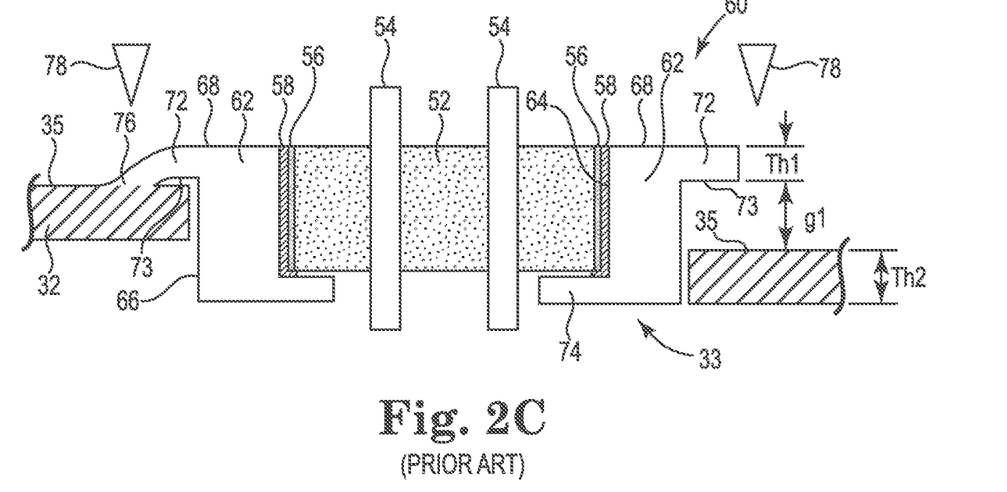
FIG. 2C is a cross-sectional view generally illustrating welding of a known feedthrough device to an implantable medical device.

FIG. 2C is a cross-sectional view of feedthrough device 50 employing known ferrule 60 and generally illustrating a scenario where exterior surface 35 of housing 32 is non-planar about opening 33. When surface 35 is non-planar, while some portions of flange 72 may be suitably positioned relative to surface 35 to form a successful lap-weld 76 therewith, such as illustrated on the left side of ferrule 60 in FIG. 2C, gaps may exist between other portions of flange 72 and housing 32, such as illustrated on the right-hand side of ferrule 60 by a gap having a gap distance, g1, between lower surface 73 of flange 72 and surface 35 of housing 32. It is noted that the gap distance, g1, represents the non-planarity of surface 35 of housing 32. If the non-planarity or gap distance, g1, is too large, a weld between flange 72 of ferrule 60 and housing 32 is likely not possible to be made or likely to fail. It has been found that a suitable weld is not likely to be made when the gap distance, g1, between lower surface 73 of flange 72 and exterior surface 35 of housing 32 is approximately 15% or more of the thickness, Th1, of flange 72.

Commonly employed thicknesses, Th1, for flange 72 are in the range of 0.02-0.04 inches (0.501-1.016 mm), and in the range of 0.012-0.016 inches (0.305-0.406 mm) for a thickness, Th2, of housing 32, with a 0.02-inch (0.501 mm) flange being employed with 0.012 inch (0.305 mm) thick housing, and a 0.04 inch (1.016 mm) flange being employed with a 0.016 inch (0.406 mm) thick housing. Using these thicknesses as an example, welds are likely to be unsuccessful when gap distance, g1, is at or exceeds approximately 0.003 inches (0.076 mm) in the case of a 0.02 inch (0.501 mm) ferrule (0.15*0.02) being used with a 0.012 inch (0.305 mm) thick housing, and 0.006 inches (0.152 mm) in the case of a 0.04 inch (1.016 mm) ferrule (0.15*0.04) being used with a 0.016 inch (0.406 mm) thick housing. In other words, to better ensure a successful lap-weld, ferrule 60 tolerates a non-planarity of up to 0.003 inches (0.076 mm) in surface 35 of a 0.012 inch (0.305 mm) thick housing 32, and up to 0.006 inches (0.152 mm) in a 0016 inch (0.406 mm) thick housing 32.

While increasing the thickness, Th1, of flange 72 may potentially increase an amount of non-planarity in housing 32 which may be tolerated by ferrule 60 while still achieving a successful weld, an amount of energy needed to form the weld when employing a thicker flange is also increased, where such increase in weld energy may, in some cases, adversely affect the braze connection 58 between ferrule 60 and insulator 52.

Figure 3:
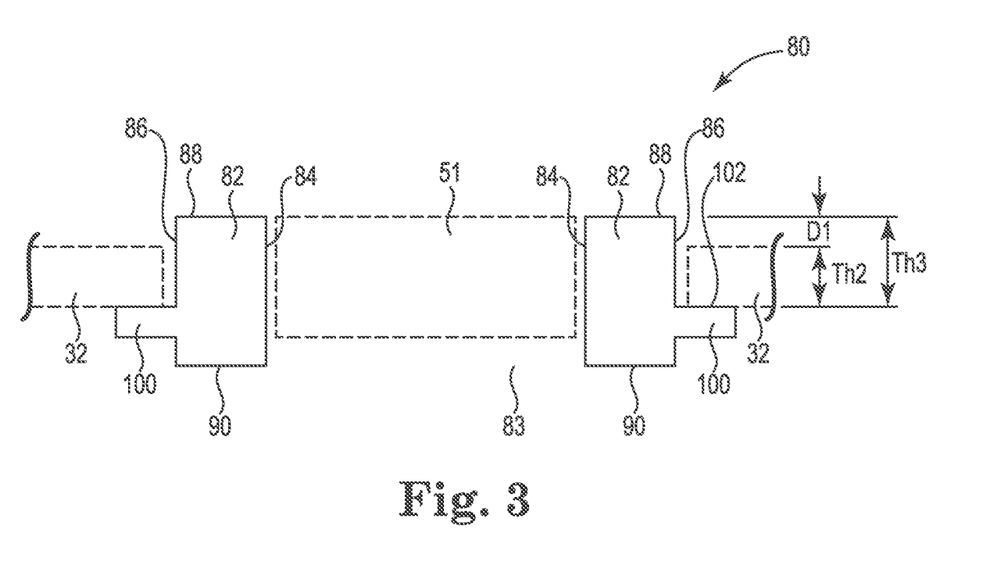
FIG. 3 is a cross-sectional view generally illustrating a ferrule, according to one example of the disclosure, for use with a feedthrough device for an implantable medical device.

FIG. 3 is a cross-sectional view illustrating an example of a ferrule 80, in accordance with the disclosure. As will be described in greater detail below, ferrule 80 increases an amount of non-planarity able to be tolerated in surface 35 of housing 32 when welding ferrule 80 to housing 32 by maintaining a relationship between thicknesses and relative positions of ferrule 80 and housing 32 and employing a butt-weld (in lieu of a lap-weld) there between.

According to one example, ferrule 80 includes a frame body 82 having an interior perimeter surface or wall 84, an exterior perimeter surface or wall 86, an upper perimeter surface 88 (to face body fluid side 38, FIG. 1), and a lower perimeter surface 90 (to face interior space 34, FIG. 1). Though not illustrated in the cross-sectional view of FIG. 3, in one example, frame body 82 is a continuous ring-like or frame-like structure having any suitable geometry (e.g., circular, oval, rectangular, etc.), with interior perimeter surface 84 defining an interior opening 83 to receive insulator assembly 51. In examples, ferrule 80 may be formed using any suitable bio-compatible material, such as titanium, for example, which is able to be mechanically attached to insulator assembly 51 (e.g., via brazing) and to housing 32 (e.g., via welding).

In accordance with the disclosure, ferrule 80 includes a housing flange 100 which extends outwardly from exterior perimeter wall 86 (away from interior opening 83) between upper and lower surfaces 88 and 90 of frame body 82 and serves as a stop for positioning housing 32 at a desired position along exterior perimeter wall 86. In one example, housing flange 100 extends perpendicularly from exterior perimeter wall 86. In one example, flange 100 is disposed along exterior surface 86 such that an upper surface 102 of flange 100 limits an upper surface 35 of housing to not more than a selected maximum offset distance, D1, below an upper surface 88 of frame body 82. In one example, the selected maximum offset distance, D1, is proportional to a thickness, Th2, of housing 32. In accordance with the disclosure, it has been found that a successful butt-weld can be made between housing 32 and exterior perimeter wall 86 when a maximum offset distance between upper surface 88 of frame body 82 and upper surface 35 of housing 32 does not exceed one-half the thickness, Th2, of housing 32. Accordingly, in one example, offset distance, D1, is approximately equal to one-half a thickness, Th2, of housing 32 (D1=0.5*Th2), such that a thickness, Th3, of frame body 82 along exterior perimeter surface 86 between upper surface 88 of frame body 82 and an upper surface 102 of housing flange 100 is approximately equal to one-and-a-half times the thickness, Th2, of housing 32 (Th3=Th2+ 0.5*Th2=1.5*Th2).

In examples, as will be described in greater detail below, such as with reference to FIGS. 4A/B and 5A/5B, for instance, by limiting a relative position (e.g., a vertical position) between upper surface 35 of housing 32 and upper surface 88 of frame body 82 along exterior perimeter surface at not more than selected maximum offset distance D1 (i.e., upper surface 35 above or below upper surface 88 by selected distance D1), a successful butt-welds is able to be made between housing 32 and exterior perimeter surface 86 of frame body 82 with a greater degree of non-planarity in surface 35 of housing 32 as compared to a known lap-type weld, such as illustrated by FIGS. 2A-2C.

Figure 4A:
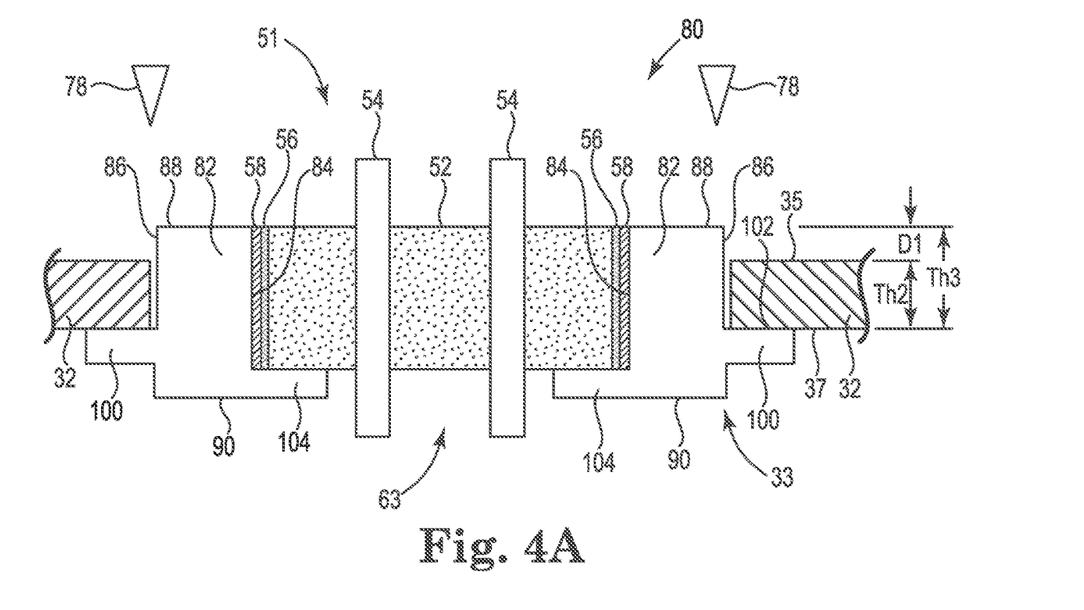
FIG. 4A is a cross-sectional view generally illustrating welding of a feedthrough device to an implantable medical device housing, according to one example.
Figure 4B:
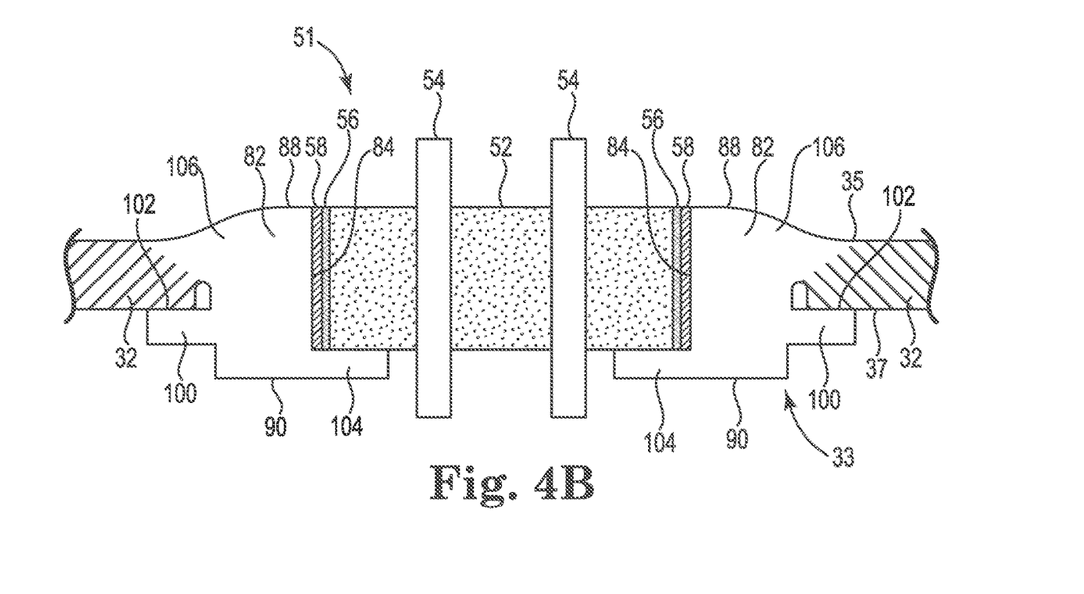
FIG. 4B is a cross-sectional view generally illustrating welding of a feedthrough device to an implantable medical device, according to one example.

FIGS. 4A and 4B are cross-sectional views illustrating the welding of a feedthrough assembly 50' employing ferrule 80, in accordance with one example of the disclosure, to housing 32 such as by laser welding (as indicated by lasers 78). In the example of FIGS. 4A and 4B, housing 32 is substantially planar, such that there negligible or no offset in the exterior surface 35 of housing 32 about opening 33 relative to flange 100 of ferrule 80. In the example of FIGS. 4A/4B, it is noted that ferrule 80 further includes a feedthrough flange 104 extending from interior perimeter surface 84 toward opening 63 to assist with connection of insulator assembly 51 to ferrule 80.

According to one example, feedthrough device 50' is positioned within opening 33 in housing 32 such that upper surface 102 of housing flange 100 faces a lower or interior surface 37 of housing 32. In one example, housing flange 100 is disposed at a position along exterior perimeter surface 86 of frame body 82 between upper and lower surfaces 88 and 90 such that upper surface 102 of housing flange 100 engages lower surface 32 of housing 32 to limit a position of upper surface 35 of housing 32 to not than more than selected maximum offset distance, D1, below upper surface 88 of frame body 82. In one example, the selected maximum offset distance D1 is approximately equal to one-half the thickness, Th2, of housing 32 (0.5*Th2), such that the distance or thickness, Th3, of frame body 82 from upper surface 102 of housing flange 100 and upper surface 88 of frame body 82 is equal to a sum of the housing thickness, Th2, and the selected maximum offset distance D1 (e.g., Th3=Th2+D1=Th2+0.5*Th2=1.5*D1).

With reference to FIG. 4B, by positioning housing 32 relative to ferrule 80 such that the maximum offset distance, D1, between exterior surface 35 of housing 32 does not exceed more than one-half the thickness, Th2, of housing 32 below the upper surface 88 of frame body 82, a successful butt-weld 106 can be achieved between ferrule 80 and housing 32 using a laser 78 having an energy level low enough so as to not damage braze joint 58 between insulator body 52 and interior perimeter surface 84 of frame body 82. If the maximum offset distance, D1, exceeds one-half the thickness, Th2, of housing 32, an energy of laser 78 needed to melt portions of frame body 82 and housing 32 to form a weld there between may result in damage to braze joint 58 and/or to housing 32.

Commonly employed thicknesses, Th2, for housing 35 are in a range from 0.012 inches to 0.016 inches (0.305-0.406 mm). With such a range, maximum offset distance, D1, of the example illustrated by FIGS. 4A/4B is in a range from 0.006-0.008 inches (0.152-0.203 mm).

Figure 5A:
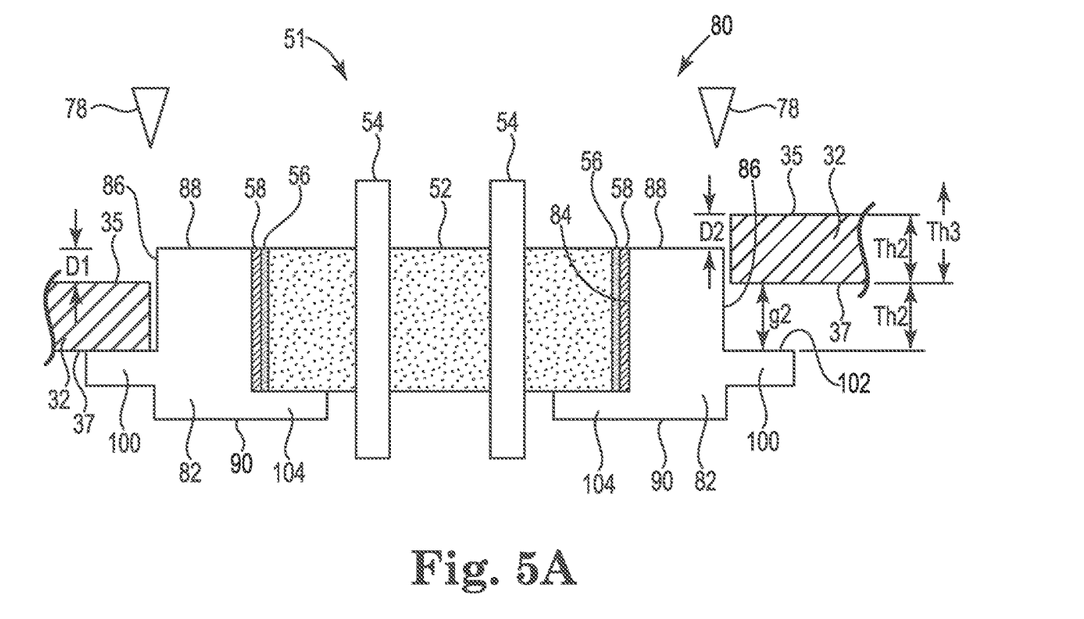
FIG. 5A is a cross-sectional view generally illustrating welding of a feedthrough device to an implantable medical device housing, according to one example.
Figure 5B:
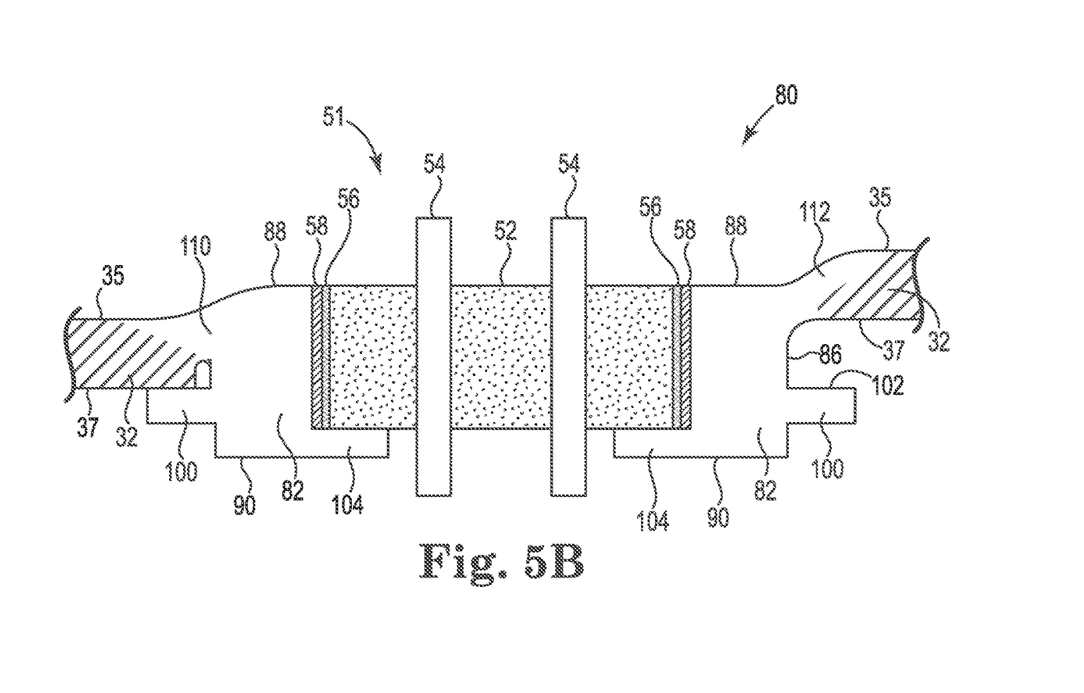
FIG. 5B is a cross-sectional view generally illustrating welding of a feedthrough device to an implantable medical device, according to one example.

FIGS. 5A and 5B are cross-sectional views illustrating the attachment of feedthrough assembly 50', according to one example, where housing 32 is non-planar about opening 33. According to one example, feedthrough device 50' is positioned within opening 33 of housing 32 such that upper face 102 of housing flange 100 engages portions of housing 32 such that upper surfaces 35 of such portions of housing 32 are offset from upper surface 88 of body 82 by maximum offset distance, D1, such as illustrated by the portion of housing 32 shown on the left-hand side of FIG. 5A.

Due to the non-planarity of housing 35, while some portions of housing 32 will be engaged by flange 102, remaining portions of housing 32 will be spaced from upper surface 102 flange 100 by a gap having a gap distance indicated as gap distance, g2, with gap distance g2 representing the non-planarity of housing 32. If gap distance, g2, exceeds one-half the thickness, Th2, of housing 32, upper surface 35 of housing 32 will extend above upper surface 88 of frame body 82 by an offset distance, D2, as illustrated in FIG. 5A.

With reference to FIG. 5B, with flange 100 positioning upper surface 35 of the portion of housing 32 on the left-hand side of ferrule 80 at maximum offset distance, D1, from upper surface 88 of frame body 82, a successful butt-weld will be achieved between housing 32 and frame body 82, as indicated by weld 110. Additionally, as long as offset distance, D2, does not exceed maximum offset distance, D1, a successful butt-weld will be achievable between frame body 82 and housing 32 on the left side of ferrule 80, as indicated by weld 112. In a case where offset distance, D2, is equal to maximum offset distance, D1, the gap distance, g2, between upper surface 102 of flange 100 and lower surface 37 of housing 32 is equal to the thickness, Th2, of housing 32, as illustrated by FIG. 5A. If offset distance, D2, exceeds maximum offset distance, D1, meaning that gap distance, g2, is greater than thickness, Th2, of housing 32, a successful butt-weld between frame body 82 and housing 32 is not likely to be achievable. In other words, as long as the non-planarity in housing 32 does not exceed the thickness, Th2, of housing 32, meaning that the gap distance, g2, does not exceed the thickness, Th2, of housing 32, ferrule 80 enables a butt-weld to be successfully made between housing 32 and frame body 82.

Thus, when welding feedthrough device 50' to housing 32, ferrule 80, in accordance with the disclosure, ferrule 80 tolerates a non-planarity in surface 35 of housing 32 which is equal to the thickness, Th2, of housing 32. As described above, commonly employed thicknesses, Th2, for housing 35 are in a range from 0.012 inches to 0.016 inches (0.305-0.406 mm). Thus, relative to ferrule 60 (see FIGS. 2A-2C), ferrule 80, in accordance with the disclosure, tolerates a non-planarity of 0.012 inches (0.305 mm) for a 0012 inch (0.030 mm) thick housing, and a non-planarity of 0.016 inches (0.406 mm) for a 0.016 inch (0.406 mm) thick housing. This represents an improvement in tolerance in non-planarity of surface 35 of housing 32 of approximately 400% for a 0.012 inch (0.305 mm) thick housing, and approximately 270% for a 0.016 inch (0.406 mm) thick housing relative to ferrule 60.

Figure 6A:
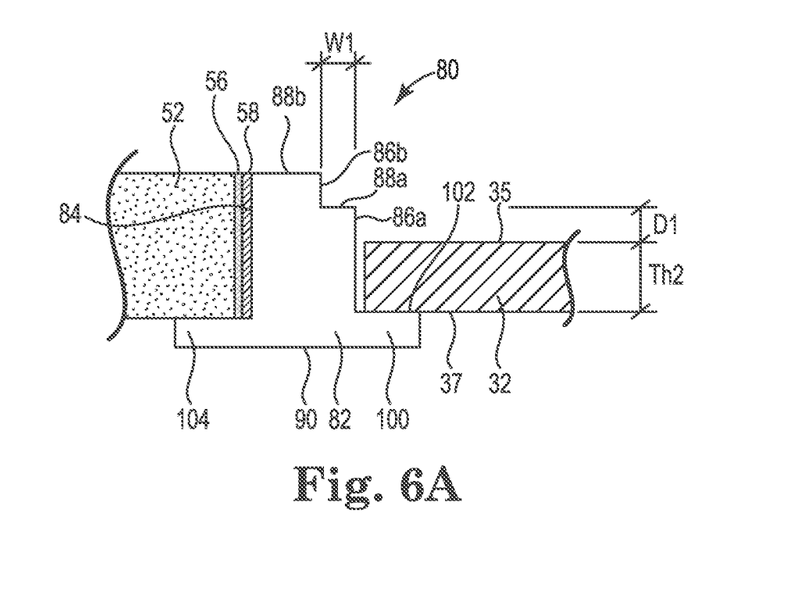
FIG. 6A is a cross-sectional view generally illustrating welding of a feedthrough device to an implantable medical device housing, according to one example.

FIGS. 6A/6B and 7A/7B generally illustrate cross-sectional views of ferrule 80, according to examples of the disclosure, where frame body 82 is stepped to lessen potential adverse impact of welding housing 32 to frame body 82 on braze joint 58 between interior perimeter surface 84 and insulator body 52.

Figure 6B:
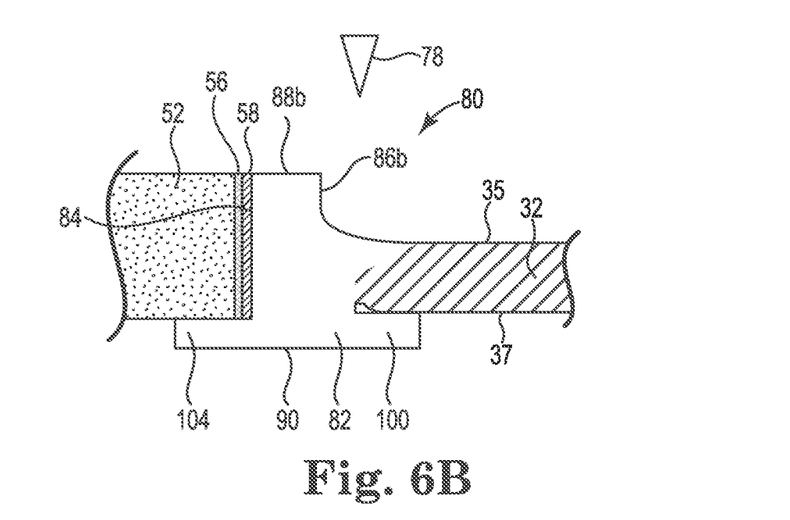
FIG. 6B is a cross-sectional view generally illustrating welding of a feedthrough device to an implantable medical device, according to one example.
Figure 6C:
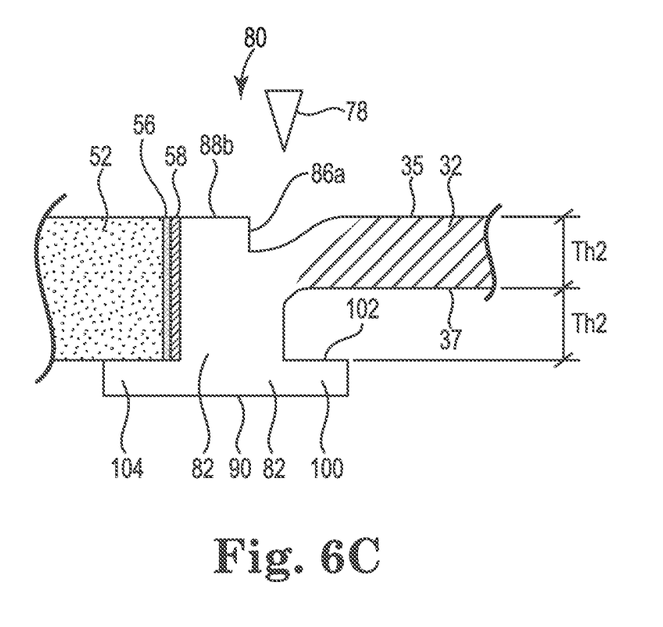
FIG. 6C is a cross-sectional view generally illustrating welding of a feedthrough device to an implantable medical device housing, according to one example.

FIGS. 6A-6C generally illustrate an example where frame body 82 is stepped such that exterior perimeter surface 86 has a first portion 86a and a second portion 86b, such that upper surface 88 includes first upper surface 88a extending between first and second portions 86a and 86b of exterior perimeter wall 86, and a second upper surface 88b extending between second portion 86b of exterior perimeter wall 86 and interior perimeter wall 84. According to the example of FIG. 6A, first upper surface 88a is disposed closer to upper surface 102 of housing flange 100 than second upper surface 88b, such that second upper surface 88b is vertically higher than first upper surface 88a relative to upper surface 102 of housing flange 100. In one example, first portion 86a of exterior perimeter wall extends vertically from upper surface 102 of flange 100 by a distance equal to the sum of the thickness, Th1, of housing 32 and the selected maximum offset distance, D1, similar to that illustrated by the FIGS. 4A and 4B. In one example, first upper surface 88a has a width, W1, not more than approximately the thickness, Th1, of housing 32.

FIGS. 6B and 6C respectively illustrate welding of housing 32 to frame body 82 when lower/interior surface 37 of housing 32 engages upper surface 102 of flange 100, and when upper surface 35 of housing 32 is disposed above first upper surface 88a by not more than the selected maximum offset distance, D1.

Figure 7A:
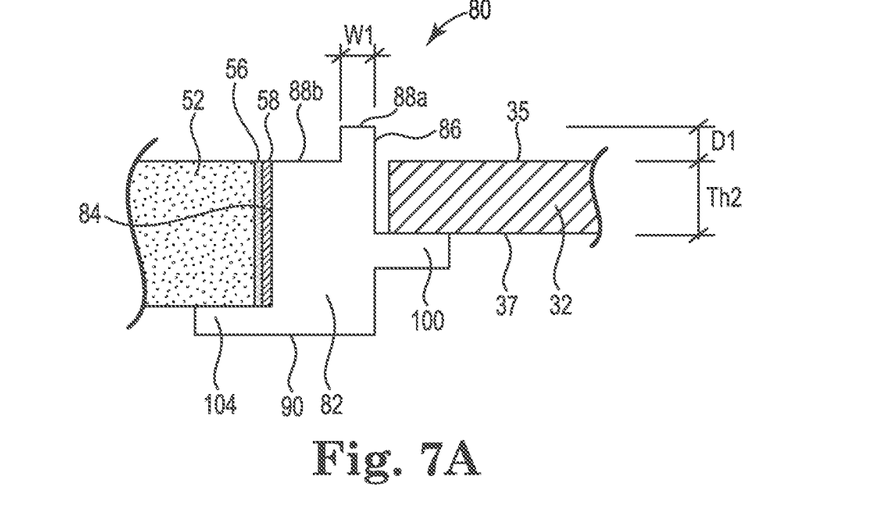
FIG. 7A is a cross-sectional view generally illustrating welding of a feedthrough device to an implantable medical device, according to one example.
Figure 7B:
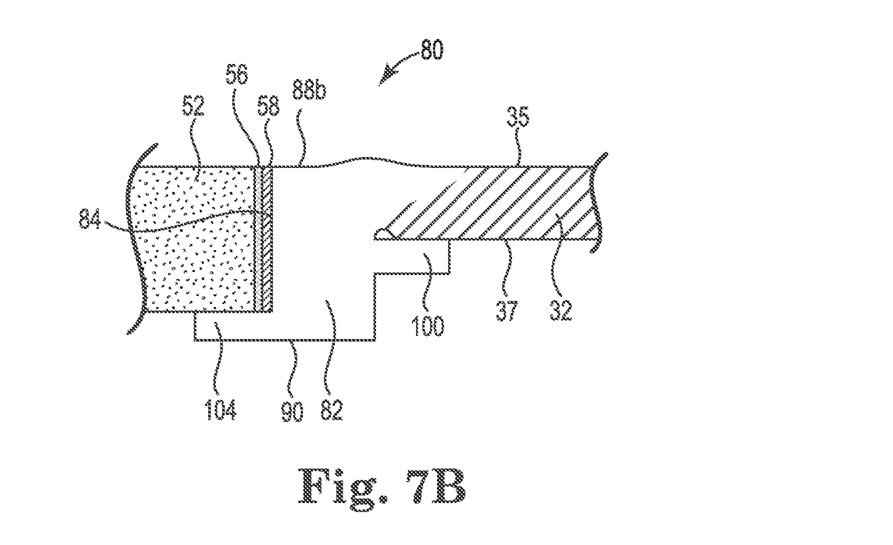
FIG. 7B is a cross-sectional view generally illustrating welding of a feedthrough device to an implantable medical device housing, according to one example.
Figure 7C:
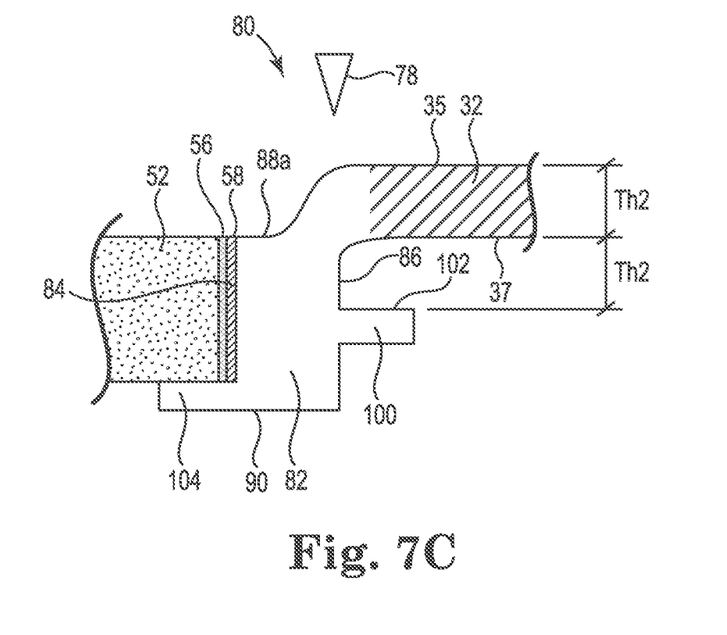
FIG. 7C is a cross-sectional view generally illustrating welding of a feedthrough device to an implantable medical device, according to one example.

FIGS. 7A-7C generally illustrate an example where frame body 82 is stepped such that upper surface 88 has a first upper surface 88a disposed adjacent to exterior perimeter surface 86, and a second upper surface 88b disposed adjacent to interior perimeter surface 84, where first upper surface 88a is disposed further away from upper surface 102 of housing flange 100 than second upper surface 88b such that exterior perimeter wall 86 extends above second upper surface 88b relative to upper surface 102 of housing flange 100.

In one example, as illustrated, exterior perimeter wall 86 extends vertically from upper surface 102 of flange 100 by a distance equal to the sum of the thickness, Th1, of housing 32 and the selected maximum offset distance, D1, similar to that illustrated by the FIGS. 4A and 4B. In one example, first upper surface 88a has a width, W1, not more than approximately the thickness, Th1, of housing 32.

FIGS. 7B and 7C respectively illustrate welding of housing 32 to frame body 82 when lower/interior surface 37 of housing 32 engages upper surface 102 of flange 100, and when upper surface 35 of housing 32 is disposed above first upper surface 88a by not more than the selected maximum offset distance, D1.

The implementations of ferrule 80 including a stepped frame body 82, as illustrated by the examples of FIGS. 6A-6C and 7A-7C provide similar improvements with regard to the increased tolerance in non-planarity of housing 32 as the examples of FIGS. 4A-4B and 5A-5B. Additionally, by employing a step in frame body 82, a potential adverse impact on braze joint 58 from thermal energy and molten material from formation of a weld joint between housing 32 and frame body 82 is reduced. In the example of FIGS. 6A-6C, molten material is less likely to reach braze joint 58, while in the example of FIGS. 7A-7C, thermal energy from welding is less like to impact braze joint 58.

Although specific embodiments have been illustrated and described herein, it will be appreciated by those of ordinary skill in the art that a variety of alternate and/or equivalent implementations may be substituted for the specific embodiments shown and described without departing from the scope of the invention. This application is intended to cover any adaptations or variations of the specific embodiments discussed herein. Therefore, it is intended that this invention be limited only by the claims and the equivalents thereof

What is claimed is:

1. A ferrule for an implantable medical device, comprising:
   a frame body including:
      an upper surface and an opposing lower surface;
      an interior perimeter surface extending between the upper and lower surfaces for attachment to an insulator assembly; and
      an exterior perimeter surface extending between the upper and lower surfaces for attachment to a housing of the implantable medical device; and
   a flange extending from the exterior perimeter surface and having an upper surface facing the upper surface of the frame body, the upper surface of the flange to engage an interior surface of the housing to limit a position of the housing along the exterior perimeter surface in a direction toward the bottom surface of the frame body, wherein a distance of the top surface of the flange from the top surface of the frame body is greater than and proportional to a thickness of the housing.

2. The ferrule of claim 1, wherein the distance of the top surface of the flange from the top surface of the frame body is up to 1.5 times the thickness of the housing.

3. The ferrule of claim 1, wherein the upper surface of the frame body is stepped such that the upper surface has a first portion intersecting with the exterior perimeter surface and a second portion intersecting with the interior perimeter surface, wherein a distance between the first portion of the upper surface of the frame body and the upper surface of the flange is up to 1.5 times the thickness of the housing.

4. The ferrule of claim 3, wherein a distance between the lower surface of the frame body and the first portion of the upper surface of the frame body is less than a distance between the lower surface of the frame body and the second portion of the upper surface of the frame body.

5. The ferrule of claim 3, wherein a distance between the lower surface of the frame body and the first portion of the upper surface of the frame body is greater than a distance between the lower surface of the frame body and the second portion of the upper surface of the frame body.

6. The ferrule of claim 3, where a width of the first portion of the upper surface of the frame body in a direction between the inner and outer perimeter surfaces is not greater than the thickness of the housing.

7. A feedthrough assembly for an implantable medical device, comprising:
   an insulator body; and
   a ferrule including:
      a frame body including:
         an upper surface and an opposing lower surface;
         an interior perimeter surface extending between the upper and lower surfaces and defining an interior opening in which the insulator body is disposed; and
         an exterior perimeter surface extending between the upper and lower surfaces for attachment to a housing; and
      a flange extending from the exterior perimeter surface and having an upper surface facing the upper surface of the frame body, the upper surface of the flange to engage an interior surface of a housing of the implantable medical device to limit a distance of an exterior surface of the housing from the upper surface of the frame body along the exterior perimeter surface in a direction toward the bottom surface of the frame body, wherein a distance between the top surface of the flange and the top surface of the frame body is greater than and proportional to a thickness of the housing.

8. The ferrule of claim 7, wherein the distance of the top surface of the flange from the top surface of the frame body is up to 1.5 times the thickness of the housing.

9. The ferrule of claim 7, wherein the upper surface of the frame body is stepped such that the upper surface has a first portion intersecting with the exterior perimeter surface and a second portion intersecting with the interior perimeter surface, wherein a distance between the first portion of the upper surface of the frame body and the upper surface of the flange is up to 1.5 times the thickness of the housing.

10. The ferrule of claim 9, wherein a distance between the lower surface of the frame body and the first portion of the upper surface of the frame body is less than a distance between the lower surface of the frame body and the second portion of the upper surface of the frame body.

11. The ferrule of claim 9, wherein a distance between the lower surface of the frame body and the first portion of the upper surface of the frame body is greater than a distance between the lower surface of the frame body and the second portion of the upper surface of the frame body.

12. The ferrule of claim 9, where a width of the first portion of the upper surface of the frame body in a direction between the inner and outer perimeter surfaces is not greater than the thickness of the housing.

13. An implantable medical device, comprising:
   a housing having an inner surface and an outer surface defining a thickness there between; and
   a feedthrough device disposed within an opening in the housing, the feedthrough device including:
      an insulator body; and
      a ferrule including:
         a frame body including:
            an upper surface and an opposing lower surface;
            an interior perimeter surface extending between the upper and lower surfaces and defining an interior opening in which the insulator body is disposed; and
            an exterior perimeter surface extending between the upper and lower surfaces and butt-welded to an edge of the housing defining the housing opening; and
         a flange extending from the exterior perimeter surface and having an upper surface facing the upper surface of the frame body, the upper surface of the flange to engage the interior surface of a housing of the implantable medical device to limit a distance of an exterior surface of the housing from the upper surface of the frame body along the exterior perimeter surface in a direction toward the bottom surface of the frame body, wherein a distance between the top surface of the flange and the top surface of the frame body is greater than and proportional to the housing thickness.

14. The ferrule of claim 13, wherein the distance of the top surface of the flange from the top surface of the frame body is up to 1.5 times the thickness of the housing.

15. The ferrule of claim 13, where a maximum distance between the interior surface of the housing and the upper surface of the flange is not greater than the housing thickness.

* * * * *